United States Patent [19]

Han

[11] Patent Number: 4,935,434
[45] Date of Patent: Jun. 19, 1990

[54] ANTIARTHRITIC ISOXAZOLE-4-CARBOXAMIDES

[75] Inventor: William T. Han, Cheshire, Conn.

[73] Assignee: Bristol-Myers Company, New York, N.Y.

[21] Appl. No.: 148,454

[22] Filed: Jan. 26, 1988

[51] Int. Cl.$^5$ .................... A61K 31/42; C07D 261/04
[52] U.S. Cl. .................. 514/378; 548/248; 560/124; 564/190
[58] Field of Search ............ 548/248; 514/378

[56] References Cited

U.S. PATENT DOCUMENTS

| 4,087,535 | 5/1978 | Heubach | 548/248 |
| 4,284,785 | 8/1981 | Hanifin, Jr. et al. | 548/248 |
| 4,284,786 | 8/1981 | Kämmerer et al. | 548/248 |

FOREIGN PATENT DOCUMENTS

| 12435 | 6/1980 | European Pat. Off. . | |
| 3247454 | 6/1984 | Fed. Rep. of Germany . | |
| 45-7054 | 3/1970 | Japan | 548/248 |
| 1596383 | 8/1981 | United Kingdom . | |

OTHER PUBLICATIONS

Doyle et al., J. Chem. Soc., 1963, p. 5845.
Hiroshi et al., Chemical Abstracts, vol. 96, No. 122673(1982).
Abstract for JP 45/7054 (3/11/70).

*Primary Examiner*—Anton H. Sutto
*Assistant Examiner*—F. Bernhardt
*Attorney, Agent, or Firm*—Mollie M. Yang

[57] ABSTRACT

Disclosed herein are isoxazole-4-carboxamides having the formula

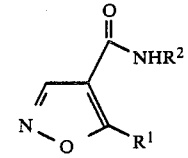

wherein $R^1$ is $C_{3-6}$ cycloalkyl and $R^2$ is selected from the group consisting of $C_{1-5}$ alkyl, $C_{2-5}$ alkenyl, $C_{2-5}$ alkynyl, $C_{3-6}$ cycloalkyl, phenyl, and phenyl substituted with at least one group selected from $C_{1-5}$ alkyl, $C_{1-5}$ alkoxy, $C_{1-5}$ alkylthio, and halo-substituted $C_{1-5}$ alkyl; with the proviso that when $R^1$ is cyclopropyl, $R^2$ is not methyl, ethyl, or cyclobutyl; or $R^1$ is $C_{1-5}$ alkyl and $R^2$ is phenylmethyl wherein the ring portion is opt. substituted with a halo-substituted $C_{1-5}$ alkyl group. These compounds have antiinflammatory and antiarthritic activities and are also useful as intermediates in the preparation of β-ketonitriles.

16 Claims, No Drawings

ANTIARTHRITIC ISOXAZOLE-4-CARBOXAMIDES

BACKGROUND OF THE INVENTION

1. Field of the Invention

The present invention relates to 5-substituted-isoxazole-4-carboxamide derivatives, to their use as antiinflammatory and antiarthritic agents, to their use as intermediates, and to pharmaceutical compositions containing them.

2. Description of Background Art

Isoxazole-4-carboxylic acid derivatives have been reported in the following references as having antiinflammatory and/or antiarthritic activities:

(a) U.S. Pat. No. 4,087,535 discloses 5-methylisoxazole-4-carboxylic acid anilides of formula (I)

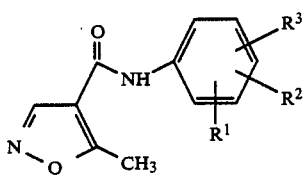

wherein $R^1$, $R^2$, and $R^3$ may each be for example $C_{1-3}$alkyl or $C_{1-3}$alkoxy where the alkyl portions may be substituted with one or more halogen atoms; $R^1$ and $R^2$ may additionally be a hydrogen atom in which case $R^3$ is not methyl. U.S. Pat. No. 4,284,786 discloses the specific compound 5-methyl-isoxazole-4-carboxylic acid, 4-(trifluoromethyl)anilide, i.e. compound of formula (I) wherein $R^1$, $R^2$ are each H, and $R^3$ is 4-trifluoromethyl.

(b) British Pat. No. 1,596,383 discloses 5-methylisoxazole-4-carboxamides of formula (II)

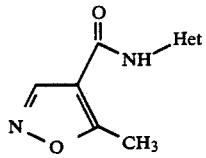

wherein Het represents an unsaturated heterocyclic radical opt. substituted with e.g. alkyl, alkoxy, or halogen.

(c) European Patent Application No. 12,435 discloses isoxazole-4-carboxamides of formula (III)

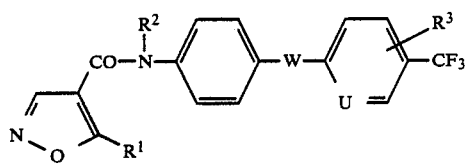

wherein $R^1$ is H, alkyl, or haloalkyl; $R^2$ is H or alkyl; $R^3$ is H or halogen; U is —CH— or nitrogen; and W is oxygen or carbonyl; or W is a direct bond in which case, $R^1$ is methyl, $R^2$, $R^3$ are each H, and U is —CH—.

(d) U.S. Pat. No. 4,284,785 discloses isoxazole-4-carboxylic acid esters and thioesters of formula (IV)

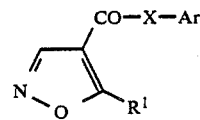

wherein X is oxygen or sulfur; $R^1$ is $C_{1-4}$alkyl; and Ar represents phenyl opt. substituted with one or more groups selected from halogen, $C_{1-4}$alkyl, $C_{1-4}$alkoxy, trifluoromethyl and trichloromethyl. These compounds are useful as intermediates in the preparation of corresponding antiinflammatory β-ketopropionitriles. Two compounds of formula (IV) wherein $R^1$ is $CH_3$, X is oxygen, and Ar is 4-methoxyphenyl or 2,4,6-trichlorophenyl also exhibit antiinflammatory activity.

(e) German Offenlegunsschrift No. 3,247,454 discloses 3-phenyl-5-methylisoxazole-4-carboxylic acid anilides of formula (V)

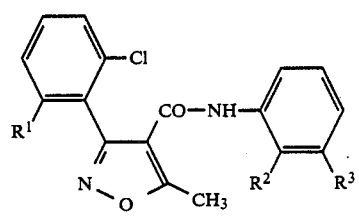

wherein $R^1$ is H, Cl, or F; $R^2$ is H or methyl; and $R^3$ is Cl, methyl, or trifluoromethyl.

5-Cyclohexyl-3-methylisoxazole-4-carboxamide (VI) has been prepared but no biological activity was reported therein (J. Chem. Soc., 1963, p 5845).

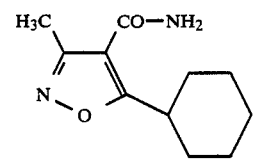

SUMMARY OF THE INVENTION

The present invention provides compounds of the formula (VII)

wherein $R^1$ is $C_{3-6}$cycloalkyl; and $R^2$ is selected from the group consisting of $C_{1-5}$alkyl, $C_{2-5}$alkenyl, $C_{2-5}$alkynyl, $C_{3-6}$cycloalkyl, phenyl, and phenyl substituted with at least one group selected from $C_{1-5}$alkyl, $C_{1-5}$alkoxy, $C_{1-5}$alkylthio, and halo-substituted $C_{1-5}$alkyl; with the proviso that when $R^1$ is cyclopropyl, $R^2$ is not methyl, ethyl, or cyclobutyl; or $R^1$ is $C_{1-5}$alkyl and $R^2$ is phenylmethyl wherein the ring portion is opt. substituted with a halo-substituted $C_{1-5}$ alkyl group.

A preferred embodiment provides compounds of formula (VII) wherein $R^1$ is cyclopropyl and $R^2$ is selected from a group consisting of $C_{3-5}$alkyl, $C_{3-5}$alkynyl and cyclopropyl.

Yet another preferred embodiment provides compounds of formula (VII) wherein $R^1$ is cyclopropyl and $R^2$ is phenyl substituted with at least one group selected from $C_{1-5}$alkoxy and halo-substituted $C_{1-5}$alkyl.

This invention also provides intermediates of formula (VIII)

wherein A is selected from the group consisting of methylamino, dimethylamino, and cyclobutylamino. Compounds of formula (VIII) are useful in the preparation of antiinflammatory compounds of formula (IX)

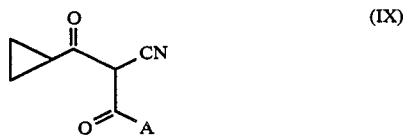

wherein A is as defined above. The preparation and antiinflammatory activity of β-cyclopropyl-α-carbamoyl-β-oxopropionitriles are described in my concurrently filed application, Ser. No. 148,540 filed Jan. 26, 1988.

A further aspect of the present invention provides a method for treatment of inflammation or arthritis which comprises administering a compound of formula (VII) to a host in need of such treatment.

Yet another aspect of the present invention provides a pharmaceutical composition which comprises an antiinflammatory or antiarthritic effective amount of a compound of formula (VII) and a pharmaceutically acceptable carrier.

DETAILED DESCRIPTION OF THE INVENTION

As used herein, the term "alkyl" includes straight and branched carbon chain.

Isoxazole-4-carboxamides of the present invention may be prepared by the process depicted in Scheme I.

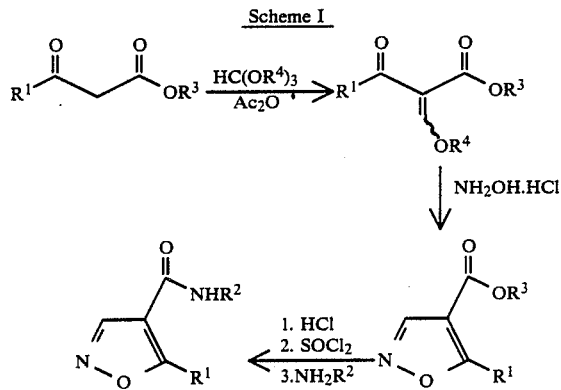

wherein $R^1$ and $R^2$ are as previously defined for formula (VII), and $R^3$ and $R^4$ are lower alkyl.

A β-substituted-β-ketopropionate is heated with an excess of a trialkyl orthoformate such as triethyl orthoformate in an acid anhydride such as acetic anhydride, preferably to the refluxing temperature of the reaction mixture, for several hours. The resultant enol ether is treated with at least an equimolar amount of hydroxylamine in an organic solvent such as ethanol at an elevated temperature, preferably the refluxing temperature of the reaction mixture, to provide the isoxazole carboxylate. The carboxylate is converted to the amide by conventional methods such as the hydrolysis of the ester group under acidic conditions, converting the resultant carboxylic acid into an acid halide using a reagent such as thionyl chloride, and finally treating the acid halide with the appropriate amine. The amine may serve as the hydrogen chloride acceptor if at least two molar equivalents are used; alternatively, a tertiary amine such as diisopropylethylamine may be used for that purpose.

Alternatively, isoxazole-4-carboxamides may be obtained from β-substituted-β-ketopropionamides using the procedure described in e.g. U.S. Pat. No. 4,987,535 and shown in Scheme II. The amide is treated with a trialkylorthoformate and the resulting alkoxymethylene derivative is cyclized using hydroxylamine.

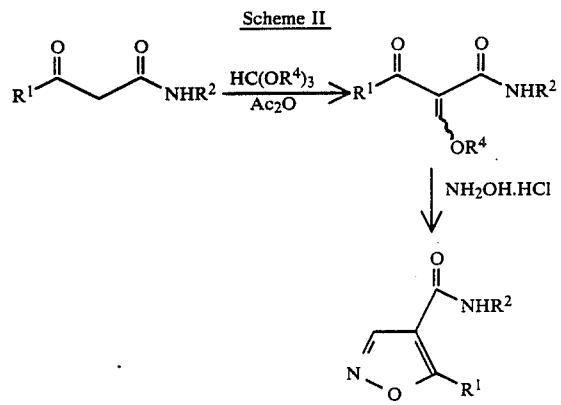

wherein $R^1$, $R^2$, and $R^4$ are as defined in Scheme I.

It is apparent that intermediates of formula (VIII) may be prepared by either the method of Scheme I or Scheme II when the appropriate starting materials are used. Base-induced ring opening yields the corresponding β-cyclopropyl-α-carbamoyl-β-oxopropionitriles (IX) which have anti-inflammatory activity. Suitable bases for the ring opening step are e.g. sodium hydroxide, sodium methoxide, sodium carbonate, and potassium hydroxide.

BIOLOGICAL ACTIVITY

Compounds of the present invention exhibit valuable pharmacological properties, in particular, anti-inflammatory and anti-arthritic activities. Representative compounds have been tested in the following in vivo models:

A. Modified developing adjuvant arthritis in rats.

This test is based on the procedure originally described by Pearson (Proc. Soc. Biol. Med., 1956, pp 91–5). Each experimental group used six male Lewis rats weighing approx. 250 gm. Arthritis was produced by a single intradermal injection of *Mycobacterium butyricum* (0.6 mg in 0.1 ml mineral oil) into the base of the tail. Test compounds were administered orally, once daily, starting on the day of inoculation (day 1) through day 8. The initial dosage was reduced during this period when side effects were observed. The paw volume (average of two hind paws) was measured by the mercury displacement method at least twice weekly during the course of the experiment (40 to 42 days). The efficacy of a compound was expressed as the percent reduction of hind paw volume of treated vs. untreated rats using the following equation:

$$\% \text{ inhibition} = \frac{PC - RX}{PC - NC} \times 100$$

PC = positive control (not treated, arthritic)
NC = negative control (not treated, non-arthritic)
RX = drug group (treated, arthritic)

B. Carrageenin induced paw edema in the rat.

This test is based on the procedure originally described by Holsapple and Yim (Inflammation, 1984, 8:223). Six male Sprague Dawley rats weighing approx. 300 gm were used in each experimental group. The rats had been starved for 24 hours prior to injection of 0.1 ml of 1% carrageenin into the plantar surface of the left hind paw. Test compounds were dosed orally 30 minutes prior to carrageenin administration. The volumes of the left hind paws were measured by mercury displacement at 2, 4, and 6 hours following carrageenin injection. The efficacy of a compound was expressed as the percent inhibition of carrageenin injected paw volume as compared to non-injected paw using the following equation:

$$\text{Percent Inhibition} = \frac{C - RX}{C} \times 100$$

C = Vehicle control group
(left paw volume − right paw volume)
RX = Drug treated group
(left paw volume − right paw volume)

The peak of drug effects usually occurred 2–4 hours following carrageenin injection.

Table I contains results of both modified developing adjuvant arthritis and carrageenin induced paw edema models.

TABLE I

Activities in adjuvant-induced polyarthritis (AIP) and carragenin-induced paw edema (CIP) models

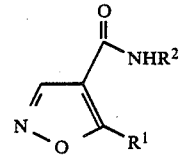

| | | | AIP % inhib.[b] | | CIP[c] |
|---|---|---|---|---|---|
| Ex. # | Compound | Dose (mg/kg)[a] | d. 20-22 | d. 40-42 | % inhib. |
| | $R^1$ = cyclopropyl $R^2$ = | | | | |
| 7 | 4-CF$_3$-phenyl | 50 (d. 1-3) | | | A |
| | | 25 (d. 4-8) | +++ | ++ | |
| 5 | 3-CF$_3$-phenyl | 50 | ++ | +++ | A |
| 6 | 4-OCH$_3$-phenyl | 100 | 0 | ++ | I |
| 3 | —CH$_2$C≡CH | 50 | ++ | ++ | I |
| 1 | —CH(CH$_3$)$_2$ | 76 | + | ++ | I |
| 4 | cyclopropyl | 89 (d. 1-5) | ++ | +++ | I |
| 2 | —C(CH$_3$)$_3$ | 50 | ++ | ++ | I |
| | $R^1$ = methyl | | | | |
| 8 | $R^2$ = 4-CF$_3$-benzyl | 100 (d. 1-2) | | | I |
| | | 50 (d. 3-4) | +++ | +++ | |

[a] once daily, p.o., from d. 1–8 (unless otherwise specified).
[b] % inhibition of paw edema: 0 = <25; + = 25-<40; ++ = 40-<60; +++ = 60-<80; ++++ = 80-100.
[c] test compound administered as a single oral dose of 50 mg/kg 30 min. prior to carrageenin injection; % inhibition determined 4 hrs. after carrageenin injection; I = <25% reduction in paw volume and A = ≧25% reduction in paw volume.

Pharmacologically active compounds of the present invention may be formulated into pharmaceutical dosage forms suitable for administration via convenient routes such as oral, intravenous, intramuscular, subcutaneous, topical and intra-articular. The formulated dosage forms may contain, in addition to the active agent, other pharmaceutically acceptable excipients to impart desirable pharmaceutical properties, for example, increased stability, improved taste, and improved appearance.

Compositions intended for oral administration may be in the form of tablets, pills, hard or soft gelatin capsules, powders, elixirs, syrups, and suspensions. Tablets, pills, powders and the like may contain additionally: a binder such as starch, gelatin, methylcellulose, or tragacanth; a disintegrant such as potato starch, alginic acid, or agar; a lubricant such as magnesium stearate, or polyethylene glycol; a diluent such as lactose, dextrose, mannitol, or cellulose; and/or other inert ingredients such as absorbants, colorants, flavoring agents, or sweeteners. Injectable compositions are preferably solutions or suspensions in a vehicle such as water, a pharmaceutically acceptable non-aqueous solvent, or a mixture thereof. They may contain, in addition to the active compound, preservatives (such as phenylmercuric nitrate, benzalkonium chloride, thimerosal, and benzyl alcohol), antioxidants (such as sodium bisulfite and acetone sodium bisulfite), emulsifiers, or buffers (such as citrates, acetates and phosphates). For intravenous administration, the unit dosage form may be diluted with conventional IV fluids such as sterile Water for Injection, NaCl Solution, or Ringer's Solution.

It will be appreciated that the actual preferred dosage of the active compounds of the present invention will vary according to the particular compound being used, the particular formulation, mode of administration, and the severity of the disease being treated. Characteristics of the afflicted host such as sex, age, body weight, liver function, kidney function, and other concurrent drug therapies may also be considered by the attending clinician. Optimal dosages for a given set of conditions can be ascertained by those skilled in the art using conventional dosage determination tests in view of the experimental animal data provided.

The following examples are illustrative of the present invention and are not to be construed as limiting its scope.

EXAMPLE 1

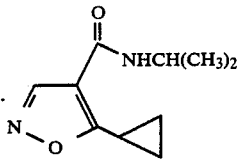

5-Cyclopropylisoxazole-4-(N-isopropyl)carboxamide

A. Ethyl β-cyclopropyl-α-ethoxymethylene-β-ketopropionate

Ethyl β-cyclopropyl-β-ketopropionate (247.0 g, 1.58 mole) [prepared according to the procedure described in J. Am. Chem. Soc., 70, 497 (1948)], triethyl orthoformate (468.3 g, 3.16 mole) and acetic anhydride (484.0 g, 4.74 mole) were combined and the solution was stirred at reflux for 4 h and at ambient temperature for 17 h. The excess reagents were distilled at water aspirator pressure (maximum head temperature permitted was 72° C.) and the oily pot residue was stirred at 10° C. with a mixture of ether and water. The ether layer was separated, washed once with cold water and dried over Na$_2$SO$_4$. Removal of the solvent gave 321.5 g (96%) of an orange-red liquid that was used directly in the next step.

B. Ethyl 5-cyclopropylisoxazole-4-carboxylate

A mixture of hydroxylamine hydrochloride (105.0 g, 1.51 mole), ethyl β-cyclopropyl-α-ethoxymethylene-β-ketopropionate (320.0 g, 1.51 mole) [prepared in Step A] and 1200 ml of EtOH was heated at reflux for 2 h. The solvent was removed in vacuo and the residue was partitioned between water and ether. The organic phase was separated, washed again with water, dried and evaporated to leave a dark, greasy solid. Trituration of the crude product under Skellysolve B gave 158 g of the title compound.

A second crop of ester (50.0 g) was obtained by evaporating the trituration solvent and chromatographing the dark residue on 300 g of silica gel using first ca. 1 L of Skellysolve B-ether (95.5) followed by 3 L of Skellysolve B-ether (9:1). Total yield 76%. An analytical sample was prepared by recrystallizing an aliquot from a warm mixture of 10:1 Skellysolve B-ether, mp 52°–55° C.

Anal. Calcd for C$_9$H$_{11}$NO$_3$: C,59.66; H, 6.12; N, 7.73. Found: C, 59.72; H, 6.24; N, 7.62.

C. 5-Cyclopropylisoxazole-4-carboxylic acid

Ethyl 5-cyclopropylisoxazole-4-carboxylate (203.0 g, 1.12 mole) [prepared in Step B] was added to a solution of 405 ml of glacial acetic acid plus 505 ml of 6N HCl and the mixture was heated in an oil bath at 105°–110° C. for 3 h. After 18 h at ambient temperature the thick mixture was diluted with water, cooled in an ice bath and filtered to give 140.8 g (82%) of the title acid. Recrystallization of an aliquot from acetonitrile gave an analytical sample, mp 163°–165° C.

Anal. Calcd for C$_7$H$_7$NO$_3$: C, 54.90; H, 4.60; N, 9.14. Found: C, 54.73; H, 4.51; N, 9.16.

D. 5-Cyclopropylisoxozole-4-carbonyl chloride

Thionyl chloride (195.8 g, 1.65 mole) was added dropwise to a stirred mixture of 5-cyclopropylisoxazole-4-carboxylic acid (140.0 g, 0.914 mole) [prepared above in Step C] and Na$_2$CO$_3$ (106.0 g, 1.0 mole) in 650 ml of ethanol-free chloroform. The mixture was heated at gentle reflux for 4 h, then the solid was filtered and the filtrate evaporated to an oil. Distillation yielded 134.8 g (86%) of the acid chloride as a colorless liquid that readily crystallized to a low melting solid, bp 123°–125° C. (13 mm).

Anal. Calcd. for C$_7$H$_6$ClNO$_2$: C, 49.00; H, 3.52; N, 8.16. Found: C, 49.67; H, 3.80; N, 8.06.

E. 5-Cyclopropylisoxazole-4-(N-isopropyl)carboxamide

A solution of isopropylamine (2.75 g, 46.6 mmoles) in 20 ml of chloroform was added dropwise at −10° C. to a solution of 5-cyclopropylisoxazole-4-carbonyl chloride (4.0 g, 23.3 mmoles) [prepared in Step D] in 60 ml of chloroform and the mixture was stirred at −10° C. to 0° C. for 30 min. The mixture was then washed twice with dilute HCl, dried and evaporated. The residual yellow oil was placed on 60 g of silica gel and chromatographed using first methylene chloride followed by methylene chloride containing 2% methanol. Recrystallization of the product from ethyl acetate/Skellysolve B yielded 2.79 g (62%) of the title compound as a white solid, mp 94°–97° C.

Anal. Calcd for C$_{10}$H$_{14}$N$_2$O$_2$: C, 61.83; H, 7.26; N, 14.43. Found: 61.57; H, 7.37; N, 14.40.

EXAMPLE 2

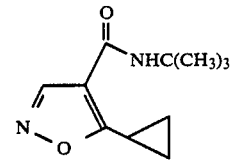

5-Cyclopropylisoxazole-4-(N-tert-butyl)carboxamide

A solution of tert-butylamine (7.25 g, 99 mmoles) in 25 ml of methylene chloride was added dropwise at 10° C. to a solution of 5-cyclopropylisoxazole-4-carbonyl chloride (8.50 g, 49.5 mmoles) [prepared in Example 1, Step D] in 100 ml of methylene chloride and the reaction mixture was stirred at ambient temperature for 1 h. The mixture was then washed twice with water (6N HCl was added if necessary to make the washes acidic), dried and evaporated. The residual solid was recrystallized from Skellysolve B-ethyl acetate (4:1) to yield 6.71 g (65%) of the title compound as a white solid, mp 116°–118.5° C.

Anal. Calcd for $C_{11}H_{16}N_2O_2$: C, 63.44; H, 7.75; N, 13.45. Found: C, 63.28; H, 7.81; N, 13.45.

EXAMPLE 3

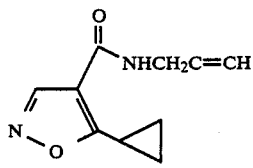

5-Cyclopropylisoxazole-4-[N-(2-propynyl)]carboxamide

The general procedure of Example 2 was repeated, except that the tert-butylamine utilized therein was replaced with 2-propynylamine. The crude product was placed on 65 g of silica gel and chromatographed using methylene chloride followed by methylene chloride-methanol (98:2). The title compound was recrystallized from ethyl acetate/Skellysolve B, mp 83°–85.5° C.

Anal. Calcd for $C_{10}H_{10}N_2O_2$: C, 63.14; H, 5.30; N, 14.73. Found: C, 63.42; H, 5.39; N, 14.86.

EXAMPLE 4

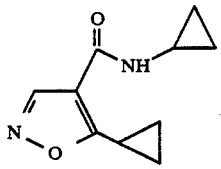

5-Cyclopropylisoxazole-4-(N-cyclopropyl)carboxamide

The general procedure of Example 2 was repeated, except that two equivalents of tert-butylamine utilized therein were replaced with one equivalent of cyclopropylamine and one equivalent of diisopropylethylamine. The crude product was purified by flash chromatography using methylene chloride followed by methylene chloride-methanol (98:2) and then recrystallized from ethyl acetate-Skellysolve B to yield the title compound, mp 102°–105° C.

Anal. Calcd for $C_{10}H_{12}N_2O_2$: C, 62.48; H, 6.29; N, 14.58. Found: C, 62.19; H, 6.36; N, 14.55.

EXAMPLE 5

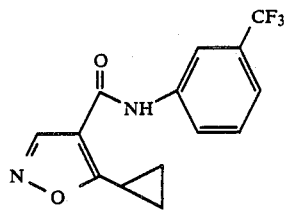

5-Cyclopropylisoxazole-4-carboxylic acid 4-(3-trifluoromethyl)anilide

A solution of 5-cyclopropylisoxazole-4-carbonyl chloride (7.9 g, 46 mmoles) [prepared in Example 1, Step D] in methylene chloride was treated dropwise at 0° C. with 3-trifluoromethylaniline (14.8 g, 92 mmoles). The resultant paste was stirred at ambient temperature for two hours and partitioned between more methylene chloride, 10% HCl and ethyl acetate. The organic layer was separated, dried and evaporated. The solid residue was placed on silica gel and chromatographed using ether-Skellysolve B (1:1). Recrystallization of the product from ether/Skellysolve B yielded 3.17 g (23%) of the title compound, mp 108.5°–111° C.

Anal. Calcd for $C_{14}H_{11}F_3N_2O_2$: C, 56.75; H, 3.74; N, 9.46. Found: C, 56.75; H, 3.73; N, 9.47.

EXAMPLE 6

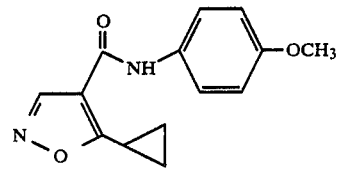

5-Cyclopropylisoxazole-4-carboxylic acid (4-methoxy)anilide

A solution of p-anisidine (10.1 g, 81.4 mmoles) in 100 ml of methylene chloride was added at 0° C. to a stirred solution of 5-cyclopropylisoxazole-4-carbonyl chloride (7.0 g, 40.7 mmoles) [prepared in Example 1, Step D] in 100 ml of methylene chloride. After 1 h the reaction solution was washed with 10% HCl dried and evaporated. The crude product was then rapidly passed through a silica gel column using 100% ether and the recovered solid was recrystallized from ethyl acetate/Skellysolve B to yield 4.4 g (41%) of the title compound, mp 127°–130° C.

Anal. Calcd for $C_{14}H_{14}N_2O_3$: C, 65.09; H, 5.46; N, 10.85. Found: C, 65.02; H, 5.60; N, 10.79.

EXAMPLE 7

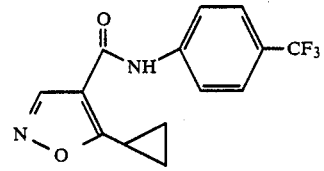

5-Cyclopropylisoxazole-4-carboxylic acid 4-trifluoromethylanilide

A. Cyclopropylcarbonylacetic acid 4-trifluoromethylanilide n-Butyllithium (5.84 ml, 15.75 mmoles of a 2.7M solution in hexane) was added at −15° C. to a solution of tetramethylpiperidine (2.22 g, 15.75 mmoles) in 40 ml of dry THF. After 10 min the cooling bath was lowered to −70° C. and cyclopropyl methyl ketone (1.26 g, 15 mmoles) was added followed in 20 min by the dropwise addition of 4-trifluoromethylphenyl isocyanate. The reaction mixture was then stirred at −70° C. for 30 min and at ambient temperature for 17 h. The solvents were evaporated and the residue was partitioned between methylene chloride and dilute HCl. The organic layer was separated, dried and concentrated to give a quantitative yield of the title compound as a greasy solid that was used directly in the next step.

B. β-Cyclopropyl-α-ethoxymethylene-β-ketopropionic acid 4-trifluoromethylanilide A mixture of cyclopropylcarbonylacetic acid 4-trifluoromethylanilide (4.07 g, 15 mmoles) [prepared in Step A], triethylorthoformate (2.45 g, 16.5 mmoles) and 4.25 ml of acetic anhydride (4.59 g, 45 mmoles) was stirred at gentle reflux for 90 min and concentrated to a dark syrup. The crude product was then placed on 100 g of silica gel and chromatographed using methylene chloride-Skellysolve B (9:1 to 95:5). The appropriate fractions were combined to give 2.36 g of solid that was recrystallized from Skellysolve B, mp 108°–113° C.

Anal. Calcd for $C_{16}H_{16}F_3NO_3$: C, 58.71; H, 4.93; N, 4.28. Found: C, 58.44, H, 4.81; N, 4.45.

C. 5-Cyclopropylisoxazole-4-carboxylic acid 4-trifluoromethylanilide

A cold solution of hydroxylamine hydrochloride (0.637 g, 9.16 mmoles) in 3.5 ml of water was neutralized with 2.30 ml of 4N NaOH, diluted with 20 ml of methanol and treated with β-cyclopropyl-α-ethoxymethylene-β-ketopropionic acid 4-trifluoromethylanilide (1.50 g, 4.58 mmoles) [prepared in Step B]. After 5 min at reduced temperature the reaction mixture was heated at reflux for 15 min. The methanol was removed at reduced pressure and the aqueous residue was extracted twice with ether. The combined extracts were washed once with water, dried and evaporated to a yellow solid. Recrystallization from 30% aqueous ethanol produced the title compound, mp 129°–130.5° C.

Anal. Calcd for $C_{14}H_{11}F_3N_2O_2$: C, 56.76; H, 3.74; N, 9.46. Found: C, 56.85; H, 3.70; N, 9.22.

EXAMPLE 8

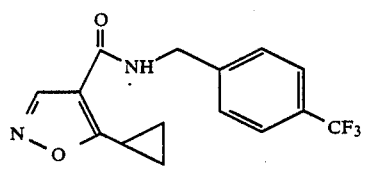

5-Methylisoxazole-4-(N-4-trifluoromethylbenzyl)carboxamide

A solution of 5-methylisoxazole-4-carbonyl chloride (1.66 g, 11.4 mmoles) [prepared according to the procedure described in U.S. Pat. No. 4,254 047] in 7 ml of acetonitrile was added dropwise to a cold solution of 4-trifluoromethylbenzylamine (2.0 g, 11.4 mmoles) and triethylamine (1.15 g, 11.4 mmoles) in 30 ml of acetonitrile. After 1 h at room temperature the mixture was filtered, concentrated to dryness and the residual solid was rubbed under water. The crude product was then recrystallized from 20% aqueous ethanol to yield 2.68 g (83%) of the title compound as a white solid, mp 156°–158° C.

Anal. Calcd for $C_{13}H_{11}F_3N_2O_2$: C, 54.93; H, 3.90; N, 9.86. Found: C, 54.90; H, 3.94; N, 9.78.

EXAMPLE 9

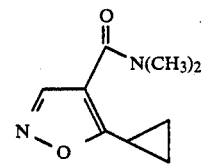

5-Cyclopropylisoxazole-4-(N,N-dimethyl)carboxamide

A solution of 5-cyclopropylisoxazole-4-carbonyl chloride (8.0 g, 46.6 mmoles) [prepared in Example 1, Step D] in 80 ml of methylene chloride was reacted with a solution of dimethylamine (4.96 g, 0.11 mole) in 44.6 ml of methylene chloride according to the general procedure of Example 1, Step E. Distillation of an aliquot of the crude product gave the title compound as a colorless oil, bp 114°–116° C. (0.03 mm).

Anal. Calcd for $C_9H_{12}N_2O_2$: C, 59.98; H, 6.71; N, 15.55. Found: C, 60.09; H. 7.02; N, 15.46.

The product from above (4.0 g, 22.2 mmoles) in a mixture of 40 ml of water plus 5 ml of methanol was treated at 10° C. with 23 ml of 1.0N sodium hydroxide and the mixture was stirred at room temperature for 90 min. The resulting solution was cooled, acidified with 6N HCl and the precipitate filtered. Recrystallization from 45% aqueous ethanol yielded 3.08 g of β-cyclopropyl-α-dimethylcarbamoyl-β-oxpropionitrile, mp 44.5°–46° C.

EXAMPLE 10

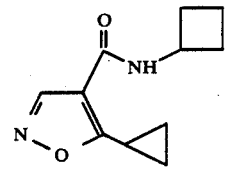

5-Cyclopropylisoxazole-4-(N-cyclobutyl)carboxamide

The general procedure of Example 1, Step E was repeated, except that the tert-butylamine utilized therein was replaced with one equivalent each of cyclobutylamine and diisopropylethylamine. The crude oil was placed on 70 g of silica gel and chromatographed using methylene chloride followed by methylene chloride containing 2% methanol. The appropriate fractions were combined and evaporated to give a waxy solid. Recrystallization from ethyl acetate/Skelly-solve B yielded the title compound, mp 103°–105° C.

Anal. calcd for $C_{11}H_{14}N_2O_2$: C, 64.06; H, 6.84; N, 13.59. Found: C, 64.17; H, 7.01; N, 13.57.

EXAMPLE 11

The general procedure of Example 1, Step E was followed using methylamine to provide 5-cyclopropylisoxazole-4-(N-methyl)carboxamide, m.p. 77°–80° C.

What is claimed is:

1. A compound having the formula

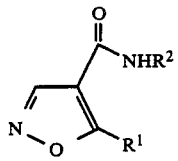

(VII)

wherein

R$^1$ is C$_{3-6}$cycloalkyl and R$^2$ is selected from the group consisting of C$_{1-5}$alkyl, C$_{2-5}$ alkenyl, C$_{2-5}$ alkynyl, C$_{3-6}$cycloalkyl, phenyl, and phenyl substituted with at least one group selected from C$_{1-5}$alkyl, C$_{1-5}$alkoxy, C$_{1-5}$alkylthio, and halo-substituted C$_{1-5}$alkyl; with the proviso that when R$^1$ is cyclopropyl, R$^2$ is not methyl, ethyl, or cyclobutyl.

2. A compound of claim 1 wherein R$^1$ is cyclopropyl.

3. A compound of claim 2 wherein R$^2$ is phenyl substituted with at least one group selected from the group consisting of C$_{1-5}$alkoxy and halo-substituted C$_{1-5}$alkyl.

4. A compound of claim 3 wherein R$^2$ is 4-trifluoromethylphenyl.

5. A compound of claim 3 wherein R$^2$ is 3-trifluoromethylphenyl.

6. A compound of claim 3 wherein R$^2$ is 4-methoxyphenyl.

7. A compound of claim 2 wherein R$^2$ is selected from the group consisting of C$_{3-5}$alkyl, C$_{3-5}$alkynyl, and cyclopropyl.

8. A compound of claim 7 wherein R$^2$ is isopropyl.

9. A compound of claim 7 wherein R$^2$ is tert-butyl.

10. A compound of claim 7 wherein R$^2$ is propargyl.

11. A compound of claim 7 wherein R$^2$ is cyclopropyl.

12. The compound 5-cyclopropylisoxazole-4-(N-methyl)carboxamide.

13. The compound 5-cyclopropylisoxazole-4-(N,N-dimethyl)carboxamide.

14. The compound 5-cyclopropylisoxazole-4(N-cyclobutyl)carboxamide.

15. A pharmaceutical composition comprising an anti-arthritic amount of a compound of claim 1 and a pharmaceutically acceptable carrier.

16. A method for treating a mammalian host suffering from arthritic condition which comprises administering to said host an anti-arthritic effective dose of a compound of claim 1.